(12) United States Patent
Janda et al.

(10) Patent No.: US 10,487,141 B2
(45) Date of Patent: Nov. 26, 2019

(54) ENANTIOPURE HAPTENS FOR NICOTINE VACCINE DEVELOPMENT

(71) Applicant: The Scripps Research Institute, La Jolla, CA (US)

(72) Inventors: Kim D. Janda, La Jolla, CA (US); Jonathan W. Lockner, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 16/215,296

(22) Filed: Dec. 10, 2018

(65) Prior Publication Data

US 2019/0119363 A1 Apr. 25, 2019

Related U.S. Application Data

(63) Continuation of application No. 15/819,283, filed on Nov. 21, 2017, now abandoned, which is a continuation of application No. 15/311,322, filed as application No. PCT/US2015/031583 on May 19, 2015, now abandoned.

(60) Provisional application No. 62/000,312, filed on May 19, 2014.

(51) Int. Cl.
*C07D 401/04* (2006.01)
*C07K 16/16* (2006.01)
*A61K 39/385* (2006.01)

(52) U.S. Cl.
CPC ............ *C07K 16/16* (2013.01); *A61K 39/385* (2013.01); *C07D 401/04* (2013.01); *C07K 2317/92* (2013.01)

(58) Field of Classification Search
CPC .................................................. C07D 401/04
USPC ...................................................... 546/276.4
See application file for complete search history.

(56) References Cited

U.S. PATENT DOCUMENTS

| | | | |
|---|---|---|---|
| 5,876,727 A | 3/1999 | Swain et al. | |
| 6,232,082 B1 | 5/2001 | Ennifar et al. | |
| 6,656,469 B1 | 12/2003 | Svensson et al. | |
| 7,446,205 B2 | 11/2008 | Ennifar | |
| 7,547,712 B2 | 6/2009 | Ennifar et al. | |
| 8,980,276 B2 | 3/2015 | Brown et al. | |
| 2007/0129551 A1 | 6/2007 | Ennifar | |
| 2011/0217320 A1 | 9/2011 | Ennifar et al. | |
| 2011/0300174 A1 | 12/2011 | Brown et al. | |
| 2013/0131015 A1 | 5/2013 | Comins et al. | |
| 2017/0107275 A1 | 4/2017 | Janda et al. | |
| 2018/0086820 A1 | 3/2018 | Janda et al. | |

FOREIGN PATENT DOCUMENTS

| | | |
|---|---|---|
| EP | 3145920 | 3/2017 |
| JP | 2002531421 A | 9/2002 |
| KR | 20170007810 | 1/2017 |
| WO | 0032239 | 6/2000 |
| WO | 2015179403 | 11/2015 |

OTHER PUBLICATIONS

"International Application Serial No. PCT US2015 031583, International Search Report dated Aug. 5, 2015", 4 pgs.
"International Application Serial No. PCT US2015 031583, Written Opinion dated Aug. 5, 2015", 8 pgs.
"International Application Serial No. PCT US2015 031583, International Preliminary Report on Patentability dated Dec. 1, 2016", 6 pgs.
"U.S. Appl. No. 15/819,283, Restriction Requirement dated Mar. 12, 2018", 8 pgs.
"U.S. Appl. No. 15/819,283, Restriction Requirement dated Jun. 28, 2018", 4 pgs.
"U.S. Appl. No. 15/819,283, Non Final Office Action dated Aug. 9, 2018", 7 pgs.
"U.S. Appl. No. 15/311,322, Non Final Office Action dated May 23, 2017", 13 pgs.
"U.S. Appl. No. 15/819,283, filed Jun. 12, 2018 to Restriction Requirement dated Mar. 12, 2018", 4 pgs.
"U.S. Appl. No. 15/819,283, filed Jul. 12, 2018 to Restriction Requirement dated Jun. 28, 2018", 5 pgs.
"European Application Serial No. 15796375.2, Extended European Search Report dated Nov. 24, 2017", 8 pgs.
"Chinese Application Serial No. 201580026158.9, Office Action dated Aug. 30, 2018", w o English translation, 8 pgs.
"European Application Serial No. 15796375.2, Communication Pursuant to Article 94(3) EPC dated Sep. 17, 2018", 3 pgs.
"Australian Application Serial No. 2015264325, First Examination Report dated Nov. 2, 2018", 4 pgs.
"European Application Serial No. 15796375.2, Response Nov. 5, 2018 to Communication Pursuant to Article 94(3) EPC dated Sep. 17, 2018", 8 pgs.
"European Application Serial No. 15796375.2, Response filed Jun. 28, 2017 to Communication pursuant to Rules 161(2) and 162 EPC dated Jan. 3, 2017", 5 pgs.
"European Application Serial No. 15796375.2, Response filed Aug. 28, 2018 to Extended European Search Report dated Nov. 24, 2017", 8 pgs.
Jacob, Nicholas T., "Investigations of Enantiopure Nicotine Haptens Using an Adjuvanting Carrier in Anti-Nicotine Vaccine Development", Journal of Medicinal Chemistry, vol. 59, No. 6, (Mar. 7, 2016), 2523-2529.
Jonathan, W Lockner, "A Conjugate Vaccine Using Enantiopure Hapten Imparts Superior Nicotine-Binding Capacity", Journal of Medicinal Chemistry, vol. 58, No. 2, (Dec. 17, 2014), 1005-1011.

(Continued)

*Primary Examiner* — Patricia L Morris
(74) *Attorney, Agent, or Firm* — Schwegman Lundberg & Woessner, P.A.

(57) ABSTRACT

The invention provides chiral haptens (−)-3'-AmNic and (−)-N4N for use in generating antibodies in a patient specific for (−)-nicotine. The haptens can be conjugated to suitable carrier proteins and administered as an antigenic mixture, optionally comprising adjuvant(s), to a patient suffering from nicotine or tobacco addiction or habituation.

7 Claims, 6 Drawing Sheets

(56) References Cited

OTHER PUBLICATIONS

Pryde, David C, "Selection of a Novel Anti-Nicotine Vaccine: Influence of Antigen Design on Antibody Function in Mice", PLOS One, vol. 8, Issue 10, e76557, (Oct. 2013), 16 pages.
"European Application Serial No. 15796375.2, Response filed Dec. 17, 2018 to Invitation pursuant to Rule 137(4) EPC and Article 94(3) EPC Nov. 14, 2018", 30 pgs.
"Chinese Application Serial No. 201580026158.9, Office Action dated May 22, 2019", w/ English Translation, 11 pgs.
"Chinese Application Serial No. 201580026158.9, Response filed Jan. 14, 2019 to Office Action dated Aug. 30, 2018", w/ English claims, 10 pgs.
"European Application Serial No. 15796375,2, Invitation pursuant to Rule 137(4) EPC and Article 94(3) EPC dated Nov. 14, 2018", 2 pgs.
"Japanese Application Serial No. 2016-568391, Notification of Reasons for Rejection dated Feb. 26, 2019", w/ English Translation, 6 pgs.
"Japanese Application Serial No. 2016-568391, Response filed May 24, 2019 to Notification of Reasons for Rejection dated Feb. 26, 2019", w/ English claims, 8 pgs.
Lockner, Jonathan W, et al., "A vaccine using enantiopure hapten imparts superior nicotine-binding capacity", (2014), 7 pgs.
Sanderson, Sam D, et al., "Immunization to nicotine with a peptide-based vaccine composed of a conformationally biased agonist of C5a as a molecular adjuvant", International Immunopharmacology 3, (2003), 137-146.

Reagents and conditions: (a) ethyl 3-iodopropionate, Zn, THF, CuCN, LiCl, trimethylacetyl chloride, −40 °C to room temperature, 20 h, 42%; (b) sulfur, xylene, reflux, 90 min, 50%; (c) NH₄OH, room temperature, 8 h, 74%; (d) Red-Al, toluene, room temperature, 90 min, 49%.

ENANTIOPURE HAPTENS FOR NICOTINE VACCINE DEVELOPMENT

CROSS-REFERENCE TO RELATED APPLICATIONS

The subject patent application is a continuation of U.S. patent application Ser. No. 15/819,283 (filed Nov. 21, 2017), which is a continuation of U.S. patent application Ser. No. 15/311,322 (filed Nov. 15, 2016), which is a § 371 U.S. national phase filing of PCT/US2015/031583 (filed May 19, 2015), which claims the benefit of priority to U.S. Provisional Patent Application No. 62/000,312 (filed May 19, 2014). The full disclosures of the applications above are incorporated by reference as if fully set forth herein.

BACKGROUND

According to the World Health Organization, there are over 1 billion smokers worldwide, and smoking is responsible for nearly 6 million deaths annually.(1) The economic impact is also sobering: in the United States alone, smoking costs nearly $300 billion in medical expenses and lost productivity each year.(2) The epidemiological link between chronic tobacco use and myriad diseases is well understood, and while many smokers wish to quit, currently available cessation aids do not help much. Synthetic small molecule agonists or antagonists target brain receptors implicated in nicotine dependence.(3-5) Acting centrally, these medicines produce an array of side effects.(6)

Meanwhile, we have been pursuing a pharmacokinetic (antibody-based) instead of a pharmacokinetic (drug-based) strategy to aiding smokers' efforts to quit.(7) Nicotine plays a central role in precipitating addiction to smoking tobacco. A nicotine vaccine stimulates the immune system to identify nicotine as a foreign antigen, eliciting antibodies that alter nicotine pharmacokinetics. Anti-nicotine antibodies reduce the concentration of free nicotine in the blood and prevent it from entering the central nervous system. Blocking the activation of brain reward systems can facilitate extinction of the addictive behavior, leading to better smoking cessation outcomes. A clinically approved nicotine vaccine would be a complementary addition to the available tools, which, when leveraged appropriately, could afford significantly better rates of sustained smoking abstinence.

NicVAX® represents the most clinically advanced nicotine vaccine to date, having progressed all the way through Phase III.(8-11) It was safe and well tolerated, but was effective for only a fraction of clinical trial participants.(12, 13) Nevertheless, given the huge promise of a clinically approved nicotine vaccine, research continues unmitigated. Many design and formulation aspects have been scrutinized in recent years to furnish something better then NicVAX®. Efforts include boosting immunogenicity through the use of newer adjuvants(14-17), improving practicality through alternative routes of administration(18), and adopting multivalent strategies(19-22) to increase anti-nicotine antibody binding capacity.

For a vaccine aimed at conferring protective immunity against a specific small molecule such as nicotine, it is important that the vaccine possess adequate chemical epitope homogeneity.(23-25) Other vaccines may be engineered to simultaneously target multiple prevailing epitopes, as in the case of diphtheria-tetanus-acellular pertussis (DTaP), measles-mumps-rubella (MMR), and 23-valent pneumococcal combination vaccines.(26, 27)

SUMMARY

The invention is directed, in various embodiments, to haptens suitable for use in raising antibodies to (−)-nicotine; to antigens comprising the haptens; to antibodies prepared using the antigens comprising the haptens; to vaccines comprising the anti-nicotine antigens; and to methods of treatment of tobacco habituation or addiction in patients comprising the use of anti-nicotine vaccines/antigens.

The haptens, in various embodiments, have sufficient structural similarity to the alkaloid (−)-nicotine, the major drug component of tobacco (*Nicotiana*), such that antibodies raised, e.g., in a human patient, against antigens comprising the haptens of the invention also react with (−)-nicotine, and thus the antigens can be suitable for administration to patients for raising anti-nicotine antibodies by means of the patient's immune system. Such antibodies can serve to bind nicotine, such as from smoked or chewed forms of tobacco, and block the drug effect on the patient that serves to reinforce the drug addiction in the patient. Furthermore, the antibodies generated by use of the antigenic vaccines of the invention can be selective for (−)-nicotine (i.e., (S)-nicotine).

In various embodiments, the invention provides a hapten of formula (−)-3'-AmNic (−)-3'-AmNic a conjugated hapten comprising (−)-3'-AmNic wherein the (−)-3'-AmNic hapten is covalently bonded via a linker to a carrier protein; an antigen for administration to a patient, comprising the conjugated hapten and optionally adjuvant(s); an antiserum produced in a patient comprising antibodies having immunological affinity for (−)-nicotine; and a method of treatment of nicotine or tobacco addiction or habituation comprising administering an effective amount of the conjugated hapten or an antigenic mixture comprising the conjugated hapten to a patient suffering from the addiction or habituation, such that antibodies are produced in the patient having affinity for (−)-nicotine.

In various embodiments, the invention provides a (−)-nicotine hapten of formula (−)-N4N (−)-N4N a conjugated hapten comprising (−)-N4N wherein the (−)-N4N hapten is covalently bonded via a linker to a carrier protein; an antigen for administration to a patient, comprising the conjugated hapten and optionally adjuvant(s); an antiserum produced in a patient comprising antibodies having immunological affinity for (−)-nicotine; and a method of treatment of nicotine or tobacco addiction or habituation comprising administering an effective amount of the conjugated hapten or an antigenic mixture comprising the conjugated hapten to a patient suffering from the addiction or habituation, such that antibodies are produced in the patient having affinity for (−)-nicotine.

DETAILED DESCRIPTION

The inventive hapten-carrier conjugates and antigen compositions specifically and selectively target only (−)-nicotine; thus, in accordance with the invention, a vaccine according to embodiments described herein efficiently elicit antibodies capable of sequestering only (−)-nicotine. The notion that antibodies can enantiodifferentiate was first appreciated by Landsteiner nearly a century ago(28, 29) and continues to be exploited to this day. Such work includes enantioselective catalytic antibodies (30-32) and stereospecific mAb to nicotine(33) and cocaine.(34-36) In the case of the nicotine mAb study, hybridomas were selected using (S)-(−)-[3H]nicotine, thereby optimizing for antibodies specific for the naturally occurring isomer.(33) The present invention exploits a capacity of antibodies to enantiodifferentiate in developing vaccines for nicotine.

Figure 1:
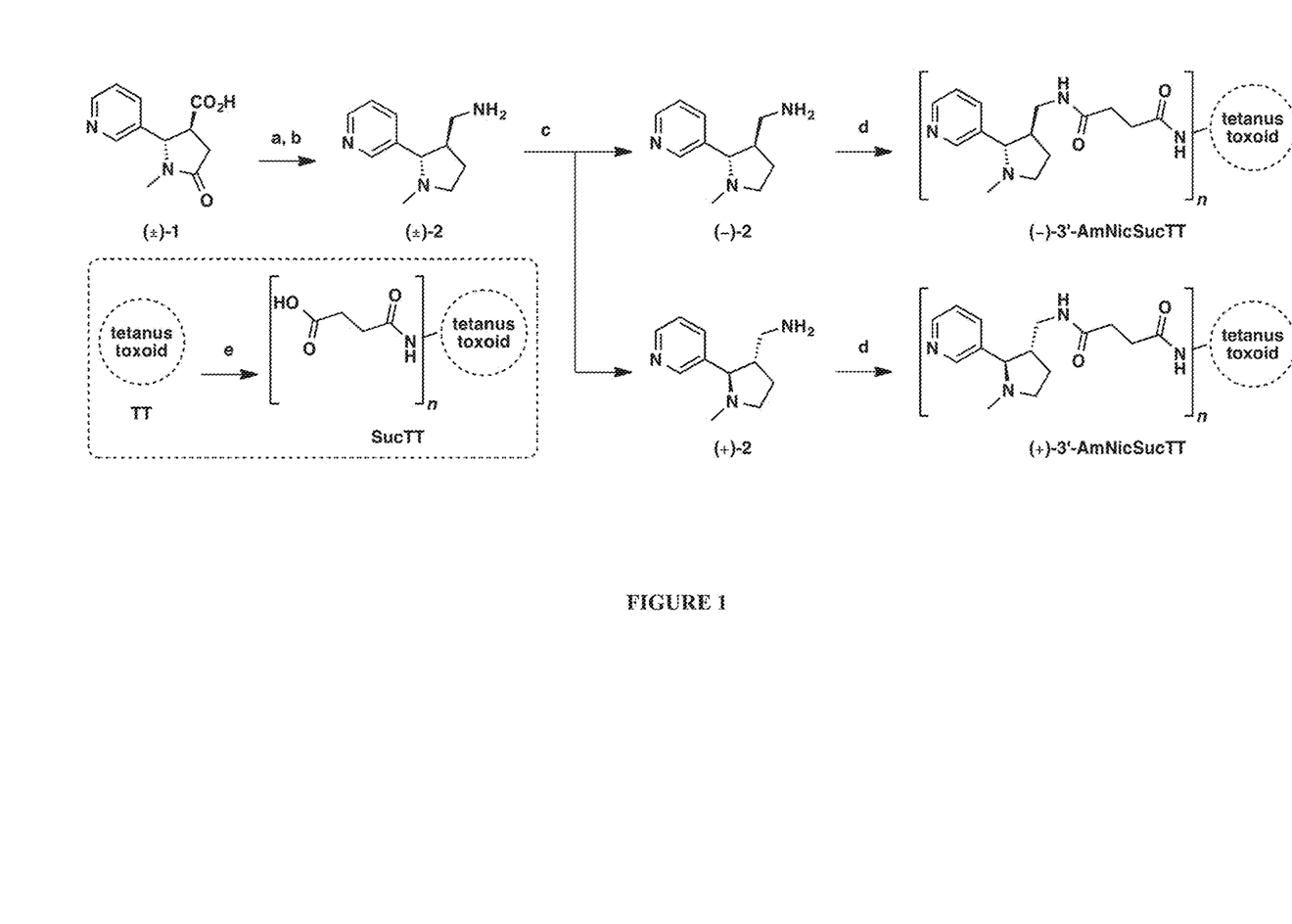
FIG. 1 shows a synthetic protocol for the preparation of (−)-3'-AmNic and (+)-3'-AmNic, which were then conjugated via a succinate linker to tetanus toxin ("TT") and evaluated for their specificity towards (−)-nicotine.

Many of the nicotine vaccines that have undergone clinical evaluation began with manipulation of racemic trans-cotinine carboxylic acid ((±)-1, FIG. 1). However, no chiral separation step (nor asymmetric synthesis step) was included in the production of the hapten-protein conjugate that would become NicVAX®. The present invention surprisingly shows that a non-racemic, fully (−)-nicotine vaccine conjugate is a superior immunogen, owing to the exquisite ability of antibodies to stereodifferentiate.

Haptens

The term "hapten" as used in the present invention is a low-molecular weight organic compound that, by itself, is incapable of eliciting an immune response. However, it will elicit an immune response once attached to a carrier molecule. According to some embodiments, the hapten is attached to the carrier via a linker.

According to one embodiment, a hapten of the present invention is a nicotine derivative that is trans-3'-aminomethylnicotine (3'AmNic). In accordance with one embodiment, for example, the hapten is a single enantiomer of trans-3'-aminomethylnicotine, specifically (−)-3'-AmNic. Both enantiomers are shown below:

(−)-3'-AmNic ((−)-2)      (+)-3'-AmNic ((+)-2)

In other embodiments, the hapten is (S)-3-(3-(1-Methyl-pyrrolidin-2-yl)pyridin-4-yl)propan-1-amine, (−)-N4N, as shown below:

(−)-N4N (6)

Figure 2:
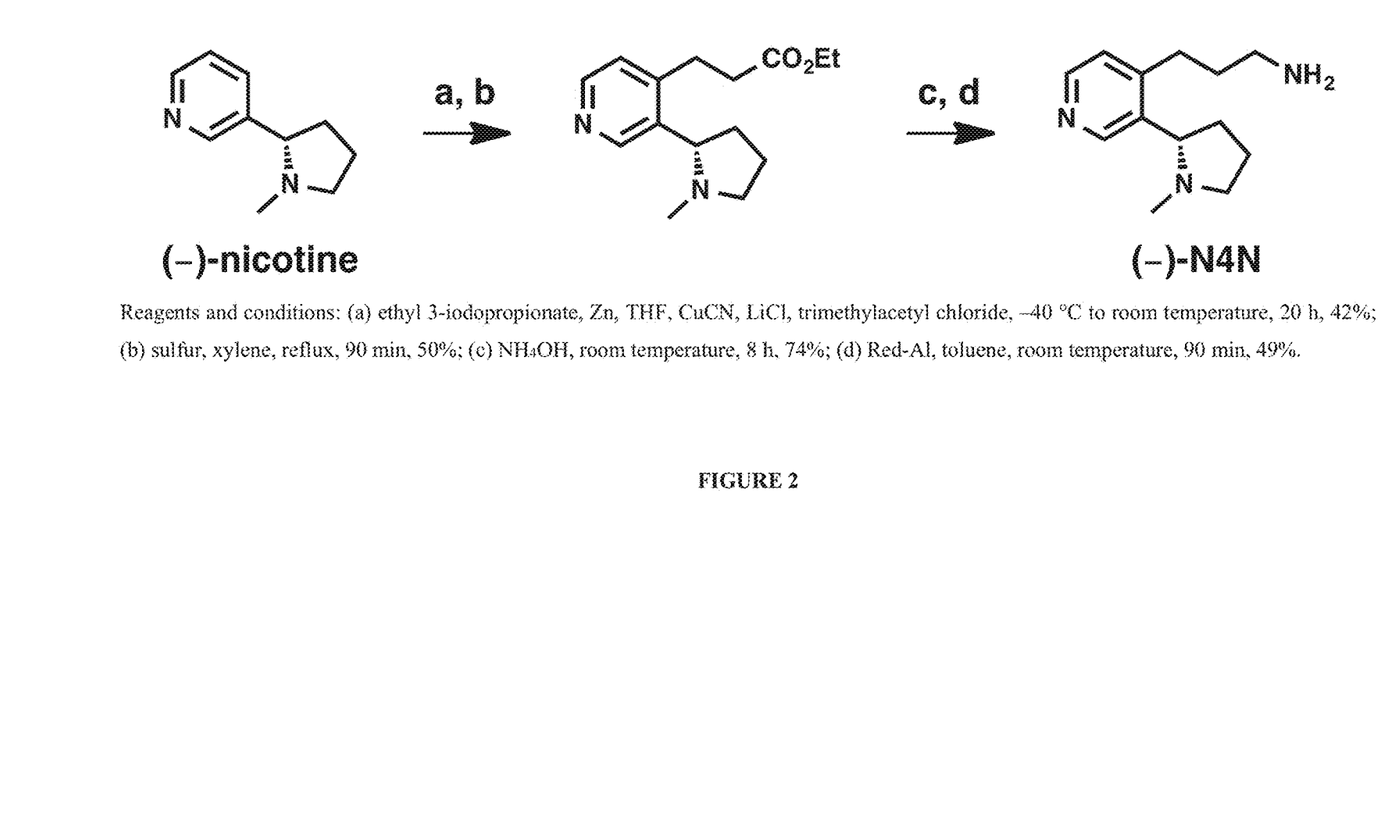
FIG. 2 shows a synthetic protocol for the preparation and conjugation of (−)-N4N.

By locating the linker attachment at the C4-position on the pyridyl ring of nicotine, no new $sp^3$ stereocenters are introduced, in contrast to the linker attachment at the 3'-position on the pyrrolidine ring in either 3'-AmNic hapten shown above. Hence, no additional stereochemical complexity is thus introduced. A further advantage of (−)-N4N arises from the use of (−)-nicotine as the starting material for the synthesis of (−)-N4N, and by performing synthetic transformations that maintain enantiopurity throughout the chemical synthesis of this nicotine hapten: the need for a chiral separation step is obviated (FIG. 2). In addition, the nature of the linker itself, methylene ($CH_2$ attached to C4-position) is superior because it does not electronically perturb nicotine's pyridyl ring the way that a heteroatom (e.g., oxygen) does at this position. Thus, both steric and stereoelectronic considerations are made, with the goal of eliciting a better anti-nicotine antibody response (higher titers or concentrations, higher affinity and specificity, superior functional antagonism of nicotine's pharmacokinetics and pharmacodynamics) by virtue of this novel nicotine hapten design.

Conjugates

According to some embodiments, a nicotine hapten is directly attached to a carrier with or without a linker. For example, a single nicotine hapten can be attached to each available amine group on a carrier protein. General methods for directly conjugating haptens to carrier proteins, using a homobifunctional or a heterobifunctional cross-linker are well known in the art, for example, by G. T. Hermanson in Bioconjugate Techniques, Academic Press (1996) and Dick and Beurret in Conjugate Vaccines. Contribu. Microbiol. Immunol., Karger, Basal (1989) vol. 10, 48-114.

Direct conjugation using bifunctional crosslinkers generally results in a molar ratio of hapten to protein being limited by the number of functional groups available on the protein for the specific conjugation chemistry. For example, a carrier protein possessing n number of lysine moieties theoretically presents n+1 primary amines (including the terminal amino) available for reaction with a linker carboxyl group. Thus, direct conjugation gives rise to formation of n+1 amido bonds, i.e., a maximum of n+1 haptens attached. The skilled person will recognize that conjugated hapten density can depend upon concentration of the reactants used to conjugate the nicotine hapten to the carrier protein, and the nature of the carrier protein. Also, within a given preparation of nicotine-carrier conjugate, there will be variation in the hapten/carrier ratio of each individual conjugate. According to some embodiments, hapten density (molar ratio of conjugated hapten to protein carrier) can range from about 10 to about 70, from about 20 to about 60, and from about 30 to about 50.

Carrier Proteins

Once the nicotine hapten is prepared, according to any of the embodiments herein described, the haptent is then conjugated to a carrier protein which will be used to raise antibodies to the nicotine carrier conjugate. In some embodiments, the carrier protein of the present invention generally is any suitable immunogenic protein or polypeptide. An "immunogenic" molecule is one that is capable of eliciting an immune response. For instance, in one embodiment, the carrier protein is a T-cell epitope.

In other embodiments, the "carrier protein" is a multi-antigenic peptide (MAP), which is a branched peptide. By using a MAP, hapten density and valency are maximized because of multiple branched amino acid residues. Examples of amino acids that can be used to form a MAP include, but are not limited to, lysine.

In some embodiments, a carrier protein comprises a molecule containing at least one T cell epitope which is capable of stimulating the T cells of the subject, which subsequently induces B cells to produce antibodies against the entire hapten-carrier conjugate molecule. The term "epitope" as used herein includes any determinant on an antigen that is responsible for its specific interaction with an antibody molecule. Epitopic determinants usually consist of chemically active surface groupings of molecules such as amino acids or sugar side chains and have specific three dimensional structural characteristics as well as specific charge characteristics.

In accordance with these embodiments and others, a carrier protein is selected based upon its ability to elicit a strong immunogenic response so that a diverse population of patients can be treated by the inventive hapten-carrier conjugates. For example, the carrier protein must be sufficiently foreign to elicit a strong immune response to the vaccine. Typically, the carrier protein in this regard is a large molecule capable of imparting immunogenicity to a covalently-linked hapten.

Many proteins known to the person skilled in conjugate vaccines are suitable for use in the present invention. For instance, in some embodiments the carrier is one that is used in the preparation of therapeutic conjugate vaccines, such as a number of toxins of pathogenic bacteria and their toxoids. Examples include diphtheria and tetanus toxins and their medically acceptable corresponding toxoids. In other embodiments, the carrier is bovine serum albumin (BSA) or keyhole limpet hemocyanin (KLH), both of which are commonly used as carriers in the development of conjugate vaccines when experimenting with animals. In still other embodiments, the protein is flagellar filament structural protein (FliC).

In accordance with still other embodiments, the carrier is a protein that is antigenically similar to bacterial toxins, often referred to as a cross-reacting materials (CRM).

Conjugation of Hapten to Carrier Protein

In accordance with some embodiments, nicotine hapten-carrier conjugates of the present invention are prepared by reacting one or more haptens with a carrier protein to yield a hapten carrier conjugate.

A variety of functional groups are used to facilitate the linking or conjugation of a carrier to a hapten of the present invention. These include functional moieties such as carboxylic acids, anhydrides, mixed anhydrides, acyl halides, acyl azides, alkyl halides, N-maleimides, imino esters, isocyanates, amines, thiols, and isothiocyanates and others that are capable of forming a covalent bond with a reactive group of a protein molecule. Depending upon the functional moiety used, according to some embodiments, the reactive group is the amino group of a lysine residue or a thiol group on a carrier protein or a modified carrier protein molecule which, when reacted, results in amide, amine, thioether, amidine urea or thiourea bond formation. Other suitable activating groups and conjugation techniques are well known in the art (Wong, Chemistry of Protein Conjugation and Cross-Linking, CRC Press, Inc. (1991). Hermanson, BIOCONJUGATE TECHNIQUES, Academic Press: 1996; and Dick and Beurret in Conjugate Vaccines. Contribu. Microbiol. Immunol., Karger, Basal (1989) vol. 10, 48-114.)

In some embodiments, the linker is a linear moiety for conjugation of haptens to carrier proteins. For example, the linker is a succinyl moiety. Another example of a linker is adipic acid dihydrazide (ADH).

Antiserum and Antibodies

The antiserum of the present invention, according to some embodiments, comprises antibodies that are produced in response to an antigen, which itself comprises a hapten-carrier conjugate as described herein. In this context, techniques for making monoclonal antibodies are well-known in the art. For instance, monoclonal antibodies can be obtained by injecting mice with a composition comprising the nicotine hapten-carrier conjugate, subsequently verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the hapten-carrier conjugate, culturing the clones that produce antibodies to the antigen, and isolating the antibodies from the hybridoma cultures.

Alternatively, monoclonal antibodies can be isolated and purified from hybridoma cultures by a variety of well-established techniques. The techniques include affinity chromatography with Protein-A Sepharose, size-exclusion chromatography, and ion-exchange chromatography (Coligan at pages 2.7.1-2.7.12 and pages 2.9.1-2.9.3; Baines et al., "Purification of Immunoglobulin G (IgG)," in METHODS IN MOLECULAR BIOLOGY, VOL. 10, pages 79-104 (The Humana Press, Inc. 1992).

Techniques for preparing polyclonal antibodies also are well-known in the art. In general, for instance, an animal is injected with immunogenic material and then antibody rich serum is collected which contains therein a mixture of antibodies that are directed against numerous epitopes of the immunogen that was injected. Suitable host mammals for the production of antibodies include, but are not limited to, humans, rats, mice, rabbits, and goats.

In accordance with some embodiments of the present invention, functional antibody fragments also can be utilized. The fragments are produced by methods that include digestion with enzymes such as pepsin or papain and/or cleavage of disulfide bonds by chemical reduction.

Alternatively, antibody fragments encompassed by the present invention can be synthesized using an automated peptide synthesizer such as those supplied commercially by Applied Biosystems, Multiple Peptide Systems and others, or they may be produced manually, using techniques well known in the art (Geysen et al., J. Immunol. Methods 102: 259 (1978)). Direct determination of the amino acid sequences of the variable regions of the heavy and light chains of the monoclonal antibodies according to the invention can be carried out using conventional techniques.

A fragment according to some embodiments of the present invention is an Fv fragment. An Fv fragment of an antibody is made up of the variable region of the heavy chain (Vh) of an antibody and the variable region of the light chain of an antibody (Vl). Proteolytic cleavage of an antibody can produce double chain Fv fragments in which the Vh and Vl regions remain non-covalently associated and retain antigen binding capacity. Fv fragments also include recombinant single chain antibody molecules in which the light and heavy chain variable regions are connected by a peptide linker (Skerra, et al. Science, 240, 1038-41 (1988)). Antibody fragments according to other embodiments of invention include Fab, Fab', $F(ab)_2$, and $F(ab')_2$, which lack the Fc fragment of an intact antibody.

Therapeutic Methods

Because nicotine exerts many of its significant effects after it crosses the blood brain barrier, the present invention provides therapeutic methods and uses for preventing nicotine from crossing the blood brain barrier. In particular, administration of a nicotine hapten-carrier conjugate to a patient generates antibodies against nicotine in the bloodstream of the patient.

Alternatively, anti-nicotine antibodies generated in a suitable host mammal and outside the body of the patient to be treated can be administered to a patient. If the patient smokes, the nicotine in his blood will be bound by the circulating anti-nicotine antibodies, preventing the nicotine from reaching the brain. Therefore, the antibodies prevent the physiological and psychological effects of nicotine that originate in the brain. Because the smoker will experience a lessening or cessation of these effects, he/she will lose the desire to smoke. The same therapeutic effects result if a patient uses smokeless tobacco, after being immunized with a nicotine hapten-carrier conjugate of the invention. Additionally, the conjugates and antibodies of the invention exert their effects by affecting the ability of nicotine to stimulate the peripheral nervous system.

Administration of Hapten-Carrier Conjugates

The conjugates of the invention are suitable for treating and preventing nicotine addiction. For treating nicotine addiction, a nicotine-carrier conjugate of the invention is administered to a patient suffering from nicotine addiction. For preventing nicotine addiction, patients at risk for developing nicotine addiction, such as teenagers, are treated with a conjugate according to the invention. Direct administration of the conjugate to a patient is called "active immunization."

A vaccine composition of the present invention comprises at least one nicotine hapten-carrier conjugate in an amount sufficient to elicit an immune response thereto. The nicotine hapten carrier conjugate is capable of remaining in vivo at a concentration sufficient to be active against subsequent intake of nicotine.

Initial vaccination with the nicotine hapten carrier conjugate of the present invention creates high titers of antibodies that are specific to nicotine. The therapeutically effective amount of a conjugate which is administered to a patient in need of treatment for nicotine addiction is readily determined by the skilled artisan. Suitable dosage ranges are 1-1000 µg/dose. It generally takes a patient one to several weeks to generate antibodies against a foreign antigen. The production of antibodies in a patient's blood can be monitored by using techniques that are well-known to the skilled artisan, such as ELISA, radioimmunoassay (RIA), and Western blotting methods. Therapeutic effectiveness also can be monitored by assessing various physical effects of nicotine, such as blood pressure.

As described in detail below, the inventive nicotine hapten-carrier conjugates can be processed to afford a composition that is administered to a patient. According to some embodiments, modes of administration include but are not limited to intranasal, intratracheal, oral, dermal, transmucosal subcutaneous injection and intravenous injection. The skilled artisan will recognize that the initial injection may be followed by subsequent administration of one or more "boosters" of conjugate. The booster increases the production of antibodies against the nicotine hapten-carrier conjugate of the invention.

In some embodiments, the vaccine or antiserum compositions of the present invention comprises at least one adjuvant. The adjuvant is selected so that the effect of the carrier protein is not inhibited. Adjuvants those which are physiologically acceptable to humans; these include, but are not limited to, alum, QS-21, saponin and MPLA (monophosphoryl lipid A).

The vaccine compositions according to other embodiments optionally comprise one or more pharmaceutically acceptable excipients. For instance, the excipients include one or more of sterile water, salt solutions such as saline, sodium phosphate, sodium chloride, alcohol, gum arabic, vegetable oils, benzyl alcohols, polyethylene glycol, gelatin, mannitol, carbohydrates, magnesium stearate, viscous paraffin, fatty acid esters, hydroxy methyl cellulose and buffers. Any additional excipients known to the skilled artisan are useful in the present invention.

The hapten-carrier conjugates of the present invention are incorporated into a pharmaceutical composition for administering to a patient in need of treatment or prevention of nicotine addiction. When the composition containing the hapten-carrier conjugate is to be used for injection, for instance, the hapten-carrier conjugate is solubilized in an aqueous, saline solution at a pharmaceutically acceptable pH. However, it is possible to use an injectable suspension of the hapten-carrier conjugate. In addition to the usual pharmaceutically acceptable excipients, the composition can contain optional components to ensure purity, enhance bioavailability and/or increase penetration.

In some embodiments, the vaccine composition optionally contains at least one auxiliary agent, such as dispersion media, coatings, microspheres, liposomes, microcapsules, lipids, surfactants, lubricants, preservatives and stabilizers. Any additional auxiliary agents known to the skilled artisan are useful in the present invention. Also useful herein are any agents which act to synergize the effect of the present vaccine composition.

The pharmaceutical composition of the present invention is sterile and is sufficiently stable to withstand storage, distribution, and use. Additionally, the composition may contain additional components in order to protect the composition from infestation with, and growth of, microorganisms. For example, the composition is manufactured in the form of a lyophilized powder that is reconstituted by a pharmaceutically acceptable diluent just prior to administration. Methods of preparing sterile injectable solutions are well known to the skilled artisan and include, but are not limited to, vacuum drying, freeze-drying, and spin drying. These techniques yield a powder of the active ingredient along with any additional excipient incorporated into the pre-mix.

Administration of Antibodies

Passive immunization comprises administration of or exposure to a polyclonal antibody or monoclonal antibody which has been raised in response to a nicotine hapten carrier conjugate of the invention. Such antibodies can be generated in animals or humans. Antibodies raised in response to a nicotine conjugate of the invention can be administered to prevent addiction to nicotine. For example, such antibodies can be administered to people considered to be at risk for developing addiction to nicotine, such as teenagers. Antibodies also are suitable for treating a patient addicted to nicotine. As discussed above, the antibodies bind nicotine in the blood, and prevent nicotine from crossing the blood brain barrier. According to some embodiments, antibodies raised by administration of the inventive hapten-carrier conjugate have a molecular weight range of from about 150 kDa to about 1,000 kDa.

The therapeutically effective amount of a therapeutic antibody of the invention which is administered to a patient in need of treatment for nicotine addiction is readily determined by the skilled artisan. Suitable dosage ranges are 1-1000 μg/dose.

A therapeutic composition according to some embodiments of the present invention comprises at least one antibody produced in response to a nicotine-carrier conjugate of the invention. The compositions optionally contain one or more pharmaceutically acceptable excipients. Useful excipients include sterile water, salt solutions such as saline, sodium phosphate, sodium chloride, alcohol, gum arabic, vegetable oils, benzyl alcohols, polyethylene glycol, gelatin, mannitol, carbohydrates, magnesium stearate, viscous paraffin, fatty acid esters, hydroxy methyl cellulose and buffers. Any additional excipients known to the skilled artisan are useful in the present invention.

The antibodies of the present invention, in order to be administered to a patient in need of treatment or prevention of nicotine addiction, are incorporated into a pharmaceutical composition. The composition comprising an antibody can be formulated in an aqueous, saline solution at a pharmaceutically acceptable pH for injection. However, it is possible to use an injectable suspension of the antibody. In addition to the usual pharmaceutically acceptable excipients, the composition contains optional components to ensure purity, enhance bioavailability and/or increase penetration.

A pharmaceutical composition comprising an antibody of the present invention is sterile and is sufficiently stable to withstand storage, distribution, and use. Additionally, the composition optionally contains additional components in order to protect the composition from infestation with, and growth of, microorganisms. Methods of preparing sterile injectable solutions are well known to the skilled artisan and include, but are not limited to, vacuum drying, freeze-drying, and spin drying. These techniques yield a powder of the active ingredient along with any additional excipient incorporated into the pre-mix.

EXAMPLES

The following examples constitute additional embodiments of the invention. The examples are therefore intended to illustrate, but not limit in any way, the invention described herein.

General Procedures

Chemistry. All reactions were carried out under an argon atmosphere with dry solvents using anhydrous conditions unless otherwise stated. Most chemicals were purchased from Sigma-Aldrich (St. Louis, Mo.) and used as received. Flagellin protein (FliC) was prepared in-house. Tetanus toxoid (TT) was purchased from Statens Serum Institut (Copenhagen, Denmark). Yields refer to chromatographically (HPLC) and spectroscopically ($^1$H NMR) homogeneous (≥95%) materials. Reactions were monitored by thin layer chromatography (TLC) carried out on 0.25 mm E. Merck silica gel plates (60F-254) using UV light as the visualizing agent. Flash column chromatography was performed using E. Merck silica gel (60, particle size 0.040-0.063 mm). Organic solvents were concentrated on a rotary evaporator under reduced pressure, followed by further evacuation using a dual stage mechanical pump. NMR spectra were recorded on a Bruker Avance III HD with DCH CryoProbe (600 MHz) instrument or a Bruker BioSpin DRX (500 MHz) instrument and calibrated using residual undeuterated solvent as an internal reference (CD$_3$OD @ δ 4.87 ppm $^1$H NMR, δ 49.00 ppm $^{13}$C NMR). The following abbreviations (or combinations thereof) are used to explain $^1$H NMR multiplicities: s=singlet, d=doublet, t=triplet, m=multiplet. High-resolution mass spectra (HRMS) were recorded on an Agilent LC/MSD TOF mass spectrometer by electrospray ionization time-of-flight reflectron experiments. IR spectra were recorded on a Thermo Scientific Nicolet 380 FTIR spectrometer.

Biology. Each hapten-protein conjugate was mixed with phosphorothioated cytosine-phosphorothioate-guanine oligodeoxynucleotide ("CpG ODN") 1826 (Eurofins MWG Operon) and diluted to 1.0 mg/mL in pH 7.4 PBS. Then, an equal volume of Alhydrogel 2% (vac-alu-50, InvivoGen) was added dropwise, followed by 10 min of gentle inversion. Vaccines prepared in this manner contained 50 μg of conjugate, 50 μg of CpG, and 20 μL of Alhydrogel per 100 μL of complete formulation.

Example 1

Synthesis of (−)-3′-AmNic

First, racemic trans-3′-aminomethylnicotine (3′-AmNic, (±)-2) was prepared from commercially available racemic trans-cotininecarboxylic acid ((±)-1). Next, using chiral supercritical fluid chromatography (SFC), ~600 mg of (±)-2 was separated into ~250 mg of each enantiomer (FIG. 1).

Example 2

(−)-3′-AmNic Tetanus Toxoid Conjugate and Vaccine

A. Conjugate. Given our prior experience (37-39) coupling carboxylate-containing nicotine haptens to carrier proteins, we tried to do the same in the present context. For this, each enantiomer of 2 prepared according to Example 1 was acylated with succinic anhydride. However, activation of succinylated haptens and mixing with tetanus toxoid ("TT") gave conjugates with low hapten densities.

Therefore, we employed an alternative choreography (Scheme 1, inset), in which the carrier protein (rather than the hapten) was first succinylated.(17, 40, 41) Hence, TT was treated with succinic anhydride in pH 8.65 Tris buffer to give SucTT. Then, SucTT was treated with 1-ethyl-3-(3-dimethylaminopropyl)carbodiimide (EDC) and either (−)- or (+)-2 in pH 5.80 2-(N-morpholino)ethane-sulfonic acid ("MES") buffer, with final dialysis against pH 7.4 PBS. This procedure yielded separate quantities of (−)- and (+)-3'-AmNicSucTT (hapten densities >40 by MALDI-TOF analysis) suitable for formulation with adjuvants as described below.

B. Vaccine. Each of the two hapten-protein conjugates as described above was mixed with phosphorothioated CpG ODN 1826(42-44) (Eurofins) and diluted to 1.0 mg/mL in pH 7.4 PBS. Then, an equal volume of Alhydrogel 2% (InvivoGen) was carefully added dropwise, followed by a brief period (10 min) of gentle inversion. Vaccines prepared in this manner contained 100 μg conjugate, 100 μg CpG, and 100 μL Alhydrogel, per 200 μL of complete formulation.(45)

Example 3

Synthesis of (S)-3-(3-(1-Methylpyrrolidin-2-yl)pyridin-4-yl)propan-1-amine ((−)-N4N,6)

A. Ethyl 3-(3-((S)-1-methylpyrrolidin-2-yl)-1-pivaloyl-1,4-dihydropyridin-4-yl)propanoate (3)

(3)

A solution of ethyl 3-iodopropionate (5.93 g, 26 mmol) in THF (40 mL) was treated with zinc powder (2.04 g, 31.2 mmol). Then, copper (I) cyanide (1.79 g, 20 mmol) and lithium chloride (1.78 g, 42 mmol) in THF (40 mL) was added. Meanwhile, in a separate flask, (−)-(S)-nicotine (3.24 g, 20 mmol) in THF (80 mL) was treated with trimethylacetyl chloride (2.41 g, 20 mmol). The contents of the two flasks were mixed and stirred overnight.

The reaction mixture was cooled to 0° C., then quenched by the addition of 10% aqueous NH$_4$OH (150 mL). The mixture was filtered, and the filtrate was concentrated in vacuo. The remaining aqueous layer was extracted with EtOAc (3×100 mL), and the combined organic layers were washed with 10% aqueous NH$_4$OH (100 mL), saturated aqueous NaHCO$_3$ (100 mL), brine (100 mL), dried over Na$_2$SO$_4$, filtered, and concentrated in vacuo. Purification by flash chromatography (silica gel, 90:10:1 EtOAc/MeOH/NH$_4$OH) afforded the title compound (2.93 g, 42%) as a pale yellow semi-solid. R$_f$=0.70 (silica gel, 90:10:1 EtOAc/MeOH/NH$_4$OH). $^1$H NMR (500 MHz, CDCl$_3$) δ 7.23 (s, 1 H), 7.12 (d, J=8.0 Hz, 1 H), 4.98 (dd J=8.0, 5.0 Hz, 1 H), 4.09 (q, J=7.3 Hz, 2 H), 1.34 (s, 9 H), 1.23 (t, J=7.0 Hz, 3 H). LCMS (ES-API) Positive mode: 349.2 [M+H$^+$] observed.

B. Ethyl (S)-3-(3-(1-methylpyrrolidin-2-yl)pyridin-4-yl)propanoate (4)

A solution of 3 (2.93 g, 8.32 mmol) in xylene (12.5 mL) at room temperature was treated with sulfur powder (0.35 g, 10.8 mmol). The resulting mixture was stirred at reflux for 90 min, and then cooled to room temperature. Purification by flash chromatography (silica gel, 90:10:0→90:10:1 EtOAc MeOH/NH$_4$OH) afforded the title compound (1.09 g, 50%) as a pale yellow oil. R$_f$=0.58 (silica gel, 90:10:1 EtOAc/MeOH/NH$_4$OH). [α]$_D$=−115° (c 2.00, EtOH). IR (neat) v$_{max}$ 2969, 2939, 2777, 1730, 1592, 1178, 1158, 1042, 831 cm$^{-1}$. $^1$H NMR (600 MHz, CDCl$_3$) δ 58.77 (s, 1 H), 8.39 (d, J=5.1 Hz, 1 H), 7.05 (d, J=5.1 Hz), 4.14 (q, J=7.1 Hz, 2 H), 3.46-3.36 (m, 1 H), 3.34-3.26 (m, 1 H), 3.00 (t, J=7.9 Hz, 2 H), 2.60 (t, J=7.9 Hz, 2 H), 2.36-2.24 (m, 2 H), 2.22 (s, 3 H), 2.06-1.95 (m, 1 H), 1.90-1.80 (m, 1 H), 1.77-1.66 (m, 1 H), 1.25 (t, J=7.2 Hz, 3 H). $^{13}$C NMR (150 MHz, CDCl$_3$) δ 172.4, 149.5, 148.0, 147.3, 136.7, 123.3, 65.6, 60.8, 57.0, 40.7, 34.7, 34.6, 26.8, 22.9, 14.3. HRMS (ESI-TOF) calcd. for C$_{15}$H$_{22}$N$_2$O$_2$H$^+$ [M+H$^+$] 263.1754, found 263.1755. LCMS (ES-API) Positive mode: 263.2 [M+H$^+$] observed.

C. (S)-3-(3-(1-Methylpyrrolidin-2-yl)pyridin-4-yl)propanamide (5)

A solution of 4 (52 mg, 0.20 mmol) in NH$_4$OH (0.5 mL) was stirred at room temperature for 8 h. The solution was concentrated in vacuo. Purification by flash chromatography (silica gel, 90:10:0→80:20:2 EtOAc/MeOH/NH$_4$OH) afforded the title compound (35 mg, 74%) as a colorless glass. R$_f$=0.17 (silica gel, 90:10:1 EtOAc/MeOH/NH$_4$OH). [α]$_D$=−1100° (c 1.14, EtOH). IR (neat) v$_{max}$ 3182, 2954, 1664, 1598, 1411, 1039, 836 cm$^{-1}$. $^1$H NMR (600 MHz, CDCl$_3$) δ 8.66 (s, 1 H), 8.37 (d, J=5.1 Hz, 1 H), 7.06 (d, J=5.0 Hz, 1 H), 5.86 (br s, 1 H), 5.52 (br s, 1 H), 3.34 (t, J=8.5 Hz, 1 H), 3.24 (t, J=7.8 Hz, 1 H), 3.12-2.96 (m, 2 H), 2.52 (t, J=7.9 Hz, 2H), 2.33-2.21 (m, 2 H), 2.17 (s, 3H), 2.01-1.92 (m, 1 H), 1.87-1.80 (m, 1 H), 1.73-1.65 (m, 1 H).

$^{13}$C NMR (150 MHz, CDCl$_3$) δ 174.0, 149.8, 148.1, 148.0, 136.5, 123.6, 66.2, 57.1, 40.8, 36.1, 34.4, 27.0, 23.0. HRMS (ESI-TOF) calcd. for C$_{13}$H$_{19}$N$_3$OH$^+$ [M+H$^+$] 234.1601, found 234.1601. LCMS (ES-API) Positive mode: 234.2 [M+H$^+$] observed.

D. (S)-3-(3-(1-Methylpyrrolidin-2-yl)pyridin-4-yl)propan-1-amine (6, (−)-N4N)

A solution of 5 (11 mg, 0.05 mmol) in toluene (0.65 mL) was treated with Red-Al (65 wt % in toluene, 64 μL, 0.21 mmol, 4.5 equiv) and stirred at room temperature for 90 min. A green reaction solution was obtained. Celite (11 mg), Darco G-60 (6 mg), and H$_2$O (110 μL) were added, and the mixture was filtered. Purification by preparative thin layer chromatography (0.5 mm silica gel plate, 4:1 CHCl$_3$/MeOH with 2% NH$_4$OH, major band R$_f$=0.4) afforded the title compound (5.1 mg, 49%) as a pale yellow oil. R$_f$=0.38 (silica gel, 4:1 CHCl$_3$/MeOH with 2% NH$_4$OH). [α]$_D$=−139° (c 1.29, EtOH). IR (neat) v$_{max}$ 3332, 3231, 2944, 2873, 2361, 1598, 1560, 1460, 1320 cm$^{-1}$. $^1$H NMR (600 MHz, CD$_3$OD) δ 8.61 (s, 1 H), 8.29 (d, J=5.1 Hz, 1 H), 7.25 (d, J=5.1 Hz, 1 H), 3.47 (t, J=8.6 Hz, 1 H), 3.24 (t, J=8.4 Hz, 1 H), 2.85-2.74 (m, 4H), 2.38-2.32 (m, 2 H), 2.18 (s, 3 H), 2.01-1.93 (m, 1 H), 1.91-1.86 (m, 1H), 1.85-1.80 (m, 2 H), 1.68-1.62 (m, 1 H). $^{13}$C NMR (150 MHz, CD$_3$OD) δ 151.6, 149.4, 148.1, 138.4, 125.6, 66.5, 57.9, 41.5, 40.8, 35.6, 32.8, 29.9, 23.5. HRMS (ESI-TOF) calcd. for C$_{13}$H$_{21}$N$_3$H$^+$ [M+H$^+$] 220.1808, found 220.1808. LCMS (ES-API) Positive mode: 220.2 [M+H$^+$] observed.

Example 4

Preparation of Hapten-Carrier Conjugates

Following the succination procedure in Example 2(A) above, each of (−)-N4N (6) and (−)-3'-AmNic ((−)2) were separately conjugated to three proteins BSA, FliC, and TT, respectively. Hapten densities of the final hapten-carrier conjugates were approximately 30 to 40.

Immunizations and Immunoassays

General. All animal care and use was performed according to NIH guidelines and in compliance with protocols approved by the Institutional Animal Care and Use Committee at The Scripps Research Institute. Male BALB/c mice (n=7 per group, 25-30 g) were obtained from the internal facility and assigned randomly to vaccine or saline groups. Mice were given free access to food and water during the immunization schedule, which consisted of three (100 μL) subcutaneous injections on days 0, 21, and 42. On days 28 and 49, serum samples were obtained by tail vein bleed. On day 63, animals were anesthetized, bled by cardiac puncture, and euthanized.

Example 5

Immunization

Following the procedures of Example 2(A) and 2(B), four hapten-protein conjugates ((−)-N4N-SucFliC, (−)-N4N-SucTT, (−)-3'-AmNic-SucFliC, and (−)-3'-AmNic-SucTT) were prepared and then evaluated as vaccine immunogens for eliciting anti-nicotine antibodies. Each conjugate was formulated with Alhydrogel and CpG ODN 1826 and administered subcutaneously to BALB/c mice on days 0, 21, and 42. Bleeds were collected on days 28, 49, and 63, as illustrated below:

Example 6

Enzyme-Linked Immunosorbent Assay (ELISA)

A. 3'-AmNic Conjugates

ELISA and cross-reactive ELISA were carried out using either (−)- or (+)-3'-AmNicSucBSA, prepared in a manner analogous to the TT conjugates described above. For ELISA, plasma samples were run against their respective haptens: rat plasma from the (−)-3'-AmNicSucTT group was assayed on (−)-3'-AmNicSucBSA plates, and rat plasma from the (+)-3'-AmNicSucTT group was assayed on (+)-3'-AmNicSucBSA plates.

For cross-reactive ELISA, plasma samples were run against their antipodes: rat plasma from the (−)-3'-AmNicSucTT group was assayed on (+)-3'-AmNicSucBSA plates, and rat plasma from the (+)-3'-AmNicSucTT group was assayed on (−)-3'-AmNicSucBSA plates.

The results of ELISA and cross-reactive ELISA are summarized in Table 1 below for the (−)-3'-AmNic and (.)-3'-AmNic derived antigens. By bleed 2 (day 49), titers were approximately 100,000. Furthermore, cross-reactive ELISA results demonstrate an approximately 3- to 5-fold difference in titers, showing that plasma antibodies produced in these two groups of rats possess a measurable level of enantiodifferentiation. Importantly, plasma from the (−)-3'-AmNicSucTT group has superior capacity to bind to natural (−)-nicotine displayed by (−)-3'-AmNicSucBSA.

TABLE 1

Summary of antibody titers from enzyme-linked immunosorbent assay (ELISA)

| Vaccine[a] | Bleed 1 | | Bleed 2 | | Bleed 3 | |
|---|---|---|---|---|---|---|
| | self-reactive | cross-reactive | self-reactive | cross-reactive | self-reactive | cross-reactive |
| (−)-3'-AmNicSucTT | 66,586 | 15,378 | 127,450 | 23,274 | 164,264 | 35,120 |
| (+)-3'-AmNicSucTT | 40,617 | 17,220 | 87,580 | 27,353 | 135,964 | 44,691 |

Figure 3:
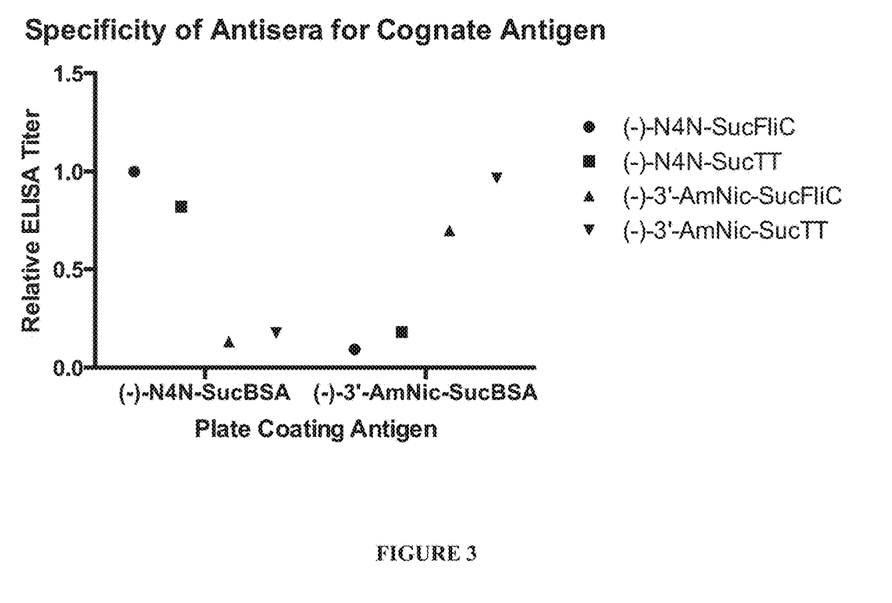
FIG. 3 depicts relative ELISA titers for antisera from vaccine groups, measured against two coating antigens. Each value depicted by a symbol is a mean (n=7). Mean titer for (−)-N4N-SucFliC antisera against (−)-N4N-SucBSA coating antigen was normalized to 1.0, and all other data points represent mean ELISA titers, relative to this antisera/coating antigen combination.

[a]formulated with CpG ODN 1826 and Alhydrogel; ELISA in duplicate (with SEM), n = 12 per group, mid-point titers B. Specificity of Antisera for Cognate Antigen (−)-N4N-SucBSA and (−)-3'-AmNic-SucBSA were used as coating antigens for ELISA. FIG. 3 depicts relative ELISA titers for antisera from each vaccine group, measured against the two coating antigens.

Example 7

Radioimmunoassay

Radioimmunoassay (RIA) provides a means for determining the average binding affinity and average antibody concentration for a soluble ligand. Because the ligand is soluble and free to associate/dissociate in the analysis milieu, it offers significant advantage over ELISA, in which the ligand is immobilized on the plate surface, not to mention conjugated to a carrier protein (e.g., BSA). Thus, the equilibrium environment simulated in an RIA experiment much more closely mimics that of free nicotine distributed in the blood and brain during tobacco use. It behooves researchers in the field to routinely incorporate RIA to evaluate the immunogenic efficacy of drug of abuse vaccine formulations.

Nicotine-specific plasma antibody binding affinities and antibody concentrations were determined by competitive (RIA) using an adaptation of the procedure described by Müller.(46) First, the plasma dilution that binds ~50% of 3H-labeled nicotine was determined. Then, the affinity constant was calculated by competition with unlabeled nicotine. Because plasma samples were pooled for each vaccine group described in Example 5 above, the measured affinity constants are average affinities for each group.

Figure 4:
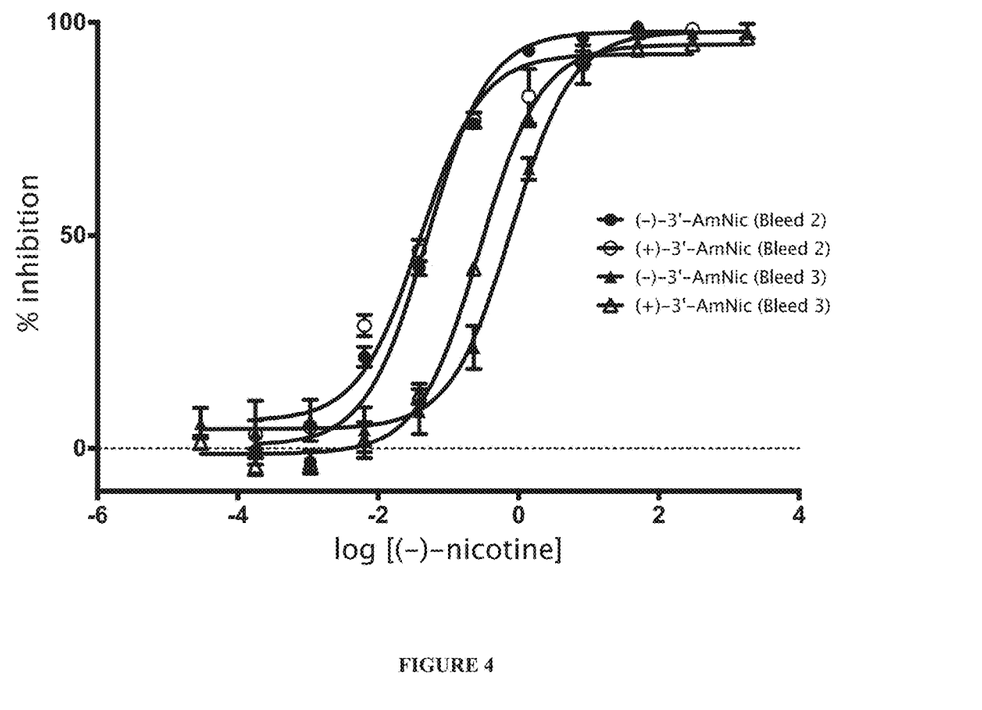
FIG. 4 shows binding affinity curves for radioimmunoassays (RIA) (−)-3'-AmNic and (+)-3'-AmNic.

As shown in FIG. 4, average binding affinity (Kdavg) and average anti-nicotine antibody concentration ([Ab]avg) were obtained, and charted in Table 2 below. By bleed 2, an approximately 4-fold difference in [Ab]avg was observed between the (−)-3'-AmNicSucTT group and the (+)-3'-AmNicSucTT group. The approximately 4-fold difference in antibody concentration observed in bleed 2 is maintained in bleed 3. It is interesting to note that ELISA/cross-reactive ELISA results showed 3- to 5-fold difference in titers; the results of these two immunoassays (ELISA and RIA) correlate with one other.

The (−)-group gave rise to superior ELISA titers and RIA antibody concentrations with a roughly 4-fold difference observed throughout. Surprisingly, affinities were higher for (−)-nicotine in the (+)-group. Scrutiny of the ELISA results and the RIA results might suggest conflicting interpretations. In particular, it seems surprising that the binding affinity for nicotine is superior (lower Kdavg) for the rats that received the (+)-vaccine. In other words, the (+)-group's plasma antibodies appear to have slightly higher binding affinity for (−)-nicotine than the (−)-group's plasma antibodies. This feature is congruent with the findings of others(47), who reported that a human anti-nicotine mAb bound (+)-nicotine with slightly higher affinity than (−)-nicotine. Incidentally, this mAb (Nic12) was derived from another clinically evaluated nicotine vaccine, NicQβ(48), which fell short in phase II.

The seemingly counterintuitive result for the measured Kdavg values may be rationalized by bearing in mind that nicotine (unlike cocaine and heroin) possesses greater conformational flexibility, since it consists of two heterocyclic rings joined via a single carbon-carbon bond. Given this flexibility, either enantiomer of nicotine can adopt an appropriate conformation suitable for making critical binding interactions with an antibody's binding site. For nicotine, these include the pyridyl nitrogen serving as a hydrogen-bond acceptor and the pyrrolidinium nitrogen engaging in charge-charge and/or cation-π interaction(s).

Linker attachment can also play a role in directing anti-hapten antibody quantity and quality. Elsewhere, it was shown that if morphine is coupled through its C-3 position to a carrier protein, codeine (3-methylmorphine) is a more effective inhibitor (than morphine) of the resultant morphine antiserum.(49) In the present study, nicotine is linked to protein carrier via the 3'-position on the pyrrolidine ring. This 3'-linkage in the (+)-3'-AmNic conjugate may impose constraints on antibody elicitation such that the measured anti-nicotine antibodies, while being of lower quantity (as anticipated), nevertheless exhibit slightly higher affinity for free (−)-nicotine than antibodies elicited by the (−)-3'-AmNic conjugate.

TABLE 2

Summary of antibody binding affinities and concentrations from radioimmunoassay

| | Bleed 2 | | | Bleed 3 | | |
|---|---|---|---|---|---|---|
| Vaccine[a] | Kdavg (nM) | [Ab]avg (μg/mL) | X (g/mol) | Kdavg (nM) | [Ab]avg (μg/mL) | X (g/mol) |
| (−)-3'-AmNicSucTT | 23.9 ± 3.2 | 47.5 ± 6.6 | 1.99 | 250 ± 22 | 118 ± 2.7 | 0.47 |
| (+)-3'-AmNicSucTT | 23.8 ± 3.2 | 12.0 ± 1.2 | 0.50 | 111 ± 9 | 30.4 ± 2.6 | 0.27 |

[a]formulated with CpG ODN 1826 and Alhydrogel; RIA in triplicate (with SEM), n = 12 per group; units for X (μg/mL/nM) were reduced to g/mol, but should not be confused with molar mass As a means for reconciling this seeming discrepancy between average antibody affinity and average antibody concentration, we propose the use of a composite parameter, X, defined as the ratio of [Ab]avg over Kdavg for a given pool of antisera. Supposing that two ways for improving vaccine performance are to elicit higher [Ab]avg (antibody abundance) and lower Kdavg (antibody utility) values, then as improvements are made in either/or/both of these terms, the ratio (X) will become larger. Thus, for Bleed 3, (−)-group's X=0.47, while (+)-group's X=0.27. The aim is to optimize protein design for a given ligand target ("antibody efficiency"); the inverse is widely applied in medicinal chemistry: optimizing a ligand design for a given protein target (e.g., "ligand efficiency"). Hence, the ratio (X) is a means for assessing antibody efficiency and, in turn, vaccine efficacy.

The data above demonstrate the importance of chirality in vaccine design, specifically the emphasis on mimicking the natural stereochemistry of a small molecule, be it (−)-cocaine, (−)-heroin, (−)-nicotine, or any other intended target. Because nicotine as a ligand can bind in a variety of orientations within the binding site of an anti-nicotine antibody, presumably as a consequence of the conformational flexibility of nicotine itself, vaccine design as well as linker placement is more nuanced in the case of nicotine. By contrast, the additional structural constraints in cocaine or in heroin impose greater conformational rigidity, and one observes unsurprising results for relative binding affinities of antibodies for natural versus unnatural enantiomers.

Example 8

Antinociception Assay

The purpose of this example is to demonstrate the antagonism of nicotine vaccines, as described above, against nicotine by measuring the latency of mouse paw withdrawal from a hot plate.

Four test groups of mice were immunized with the four vaccines, respectively, and according to the immunization schedule as described above in Example 5. A fifth and vaccine-naïve group of mice received saline injections during the immunization schedule. All five groups of mice were then administered nicotine and then assayed on a hot plate to measure the latency in paw withdrawal from the hot plate is measured.

Antinociception for each nicotine vaccine was expressed as a percentage of maximum possible effect ("% MPE"). % MPE=(test−baseline)/(cutoff−baseline)×100, where "test" is the latency to respond after treatment; "baseline" is the latency to respond prior to treatment; and "cutoff" is the preset time at which the test was ended in the absence of a response. A baseline measure was obtained for each animal in the five groups prior to the immunization schedule above.

Figure 5:
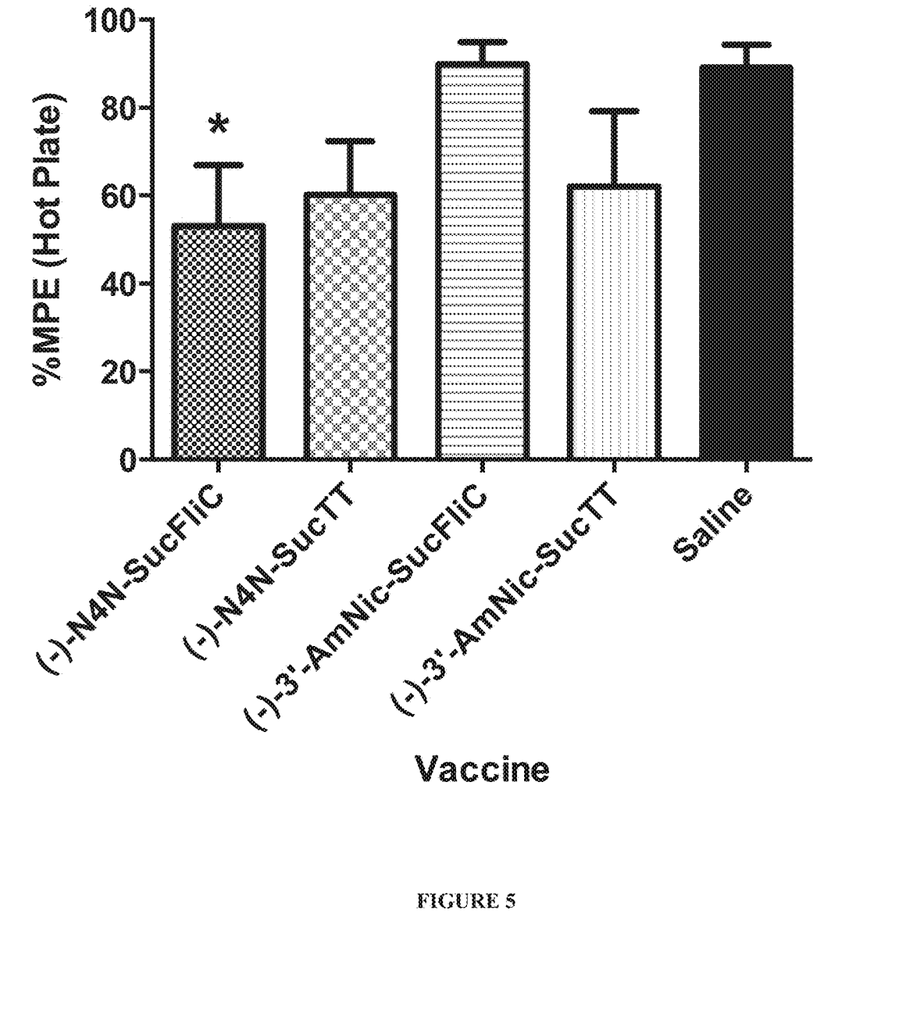
FIG. 5 is a graph summarizing results from an antinociception assay of four nicotine vaccines relative to saline control in mice. Each bar depicted is a mean (n=7) with error bar as SEM. Ordinary one-way ANOVA with uncorrected Fisher's LSD, * P<0.05 for (−)-N4N-SucFliC vs. Saline.

The results are summarized in FIG. 5, showing efficacy of the nicotine vaccines, relative to saline, in antagonizing the pain-relieving effects of nicotine in subject groups of mice.

Example 8

Hypothermia Assay

Figure 6:
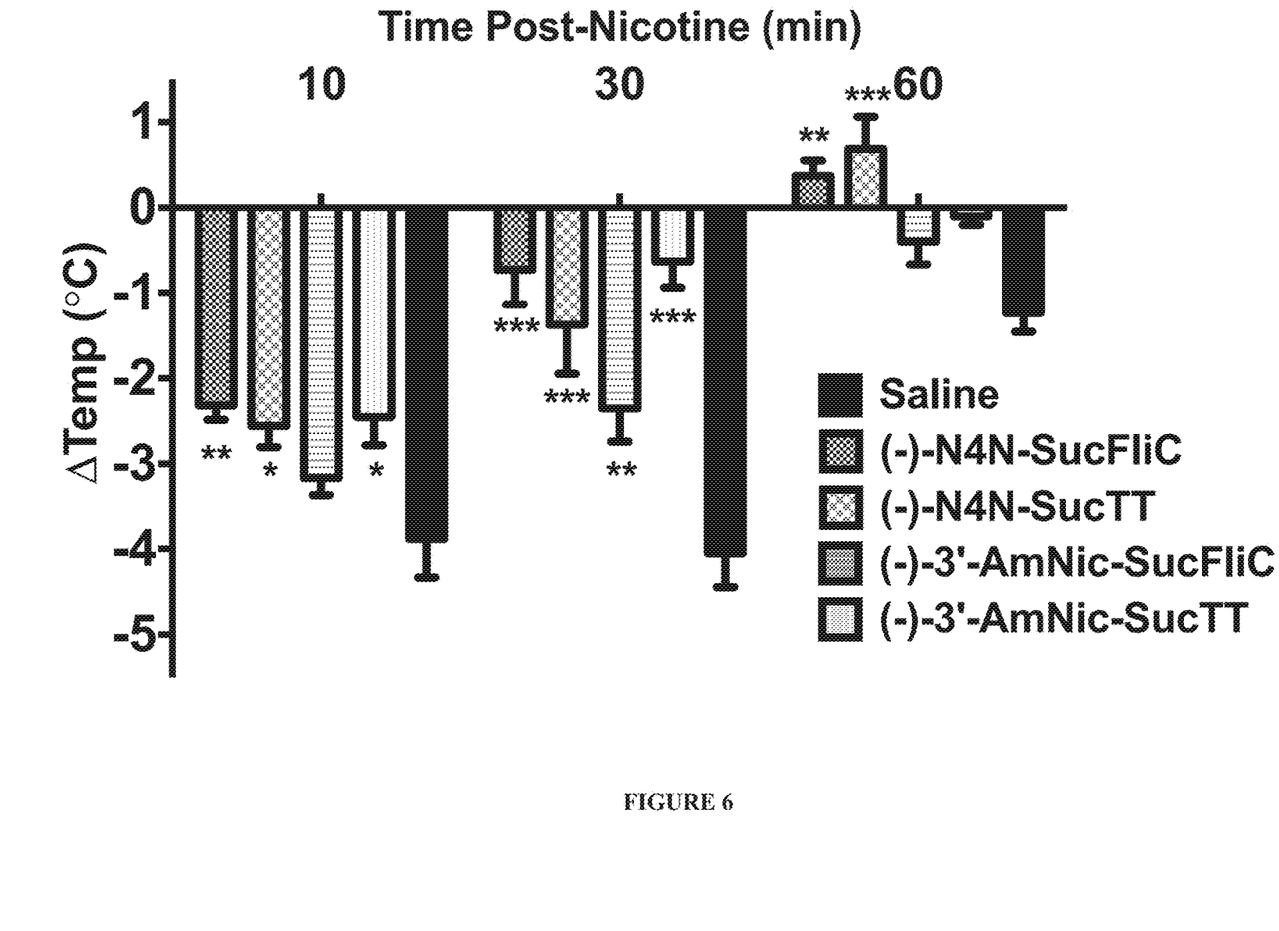
FIG. 6 summarizes results from a hypothermia assay for measuring efficacy of four nicotine vaccines in attenuating the effect of nicotine in mice. Each bar depicted is a mean (n=7) with error bar as SEM. Two-way RM ANOVA with Dunnett's multiple comparisons test, * P<0.05 for annotated vaccine group vs. Saline,  P<0.005 for annotated vaccine group vs. Saline, * P<0.0001 for annotated vaccine group vs. Saline.

Body temperatures of mice in the five groups described above in Example 7 were measured at 10 minutes, 30 minutes, and 60 minutes following administration of nicotine. The four tested nicotine vaccines antagonized the effect of nicotine by attenuating body temperature depression, relative to the saline control group that experienced the most pronounced depression of temperature. Results are summarized in FIG. 6.

DOCUMENTS CITED (1) World Health Organization. WHO Report on the Global Tobacco Epidemic, 2011; World Health Organization: Geneva: World Health Organization, 2011.
(2) U.S. Department of Health and Human Services. The Health Consequences of Smoking-50 Years of Progress: A Report of the Surgeon General; Atlanta: U.S. Department of Health and Human Services, Centers for Disease Control and Prevention, National Center for Chronic Disease Prevention and Health Promotion, Office on Smoking and Health, 2014.
(3) Aubin, H. J.; Karila, L.; Reynaud, M. Pharmacotherapy for smoking cessation: present and future. Curr. Pharm. Des. 2011, 17, 1343-50.
(4) Harmey, D.; Griffin, P. R.; Kenny, P. J. Development of novel pharmacotherapeutics for tobacco dependence: progress and future directions. Nicotine Tob. Res. 2012, 14, 1300-18.
(5) Aubin, H. J.; Luquiens, A.; Berlin, I. Pharmacotherapy for smoking cessation: pharmacological principles and clinical practice. Br. J. Clin. Pharmacol. 2014, 77, 324-36.
(6) Hays, J. T.; Ebbert, J. O. Adverse effects and tolerability of medications for the treatment of tobacco use and dependence. Drugs 2010, 70, 2357-72.
(7) Gorelick, D. A. Pharmacokinetic strategies for treatment of drug overdose and addiction. Future Med. Chem. 2012, 4, 227-43.
(8) Hatsukami, D. K.; Rennard. S.; Jorenby, D.; Fiore, M.; Koopmeiners, J.; de Vos. A.; Horwith, G.; Pentel, P. R. Safety and immunogenicity of a nicotine conjugate vaccine in current smokers. Clin. Pharmacol. Ther. 2005, 78, 456-67.
(9) Wagena, E. J.; de Vos, A.; Horwith, G.; van Schayck, C. P. The immunogenicity and safety of a nicotine vaccine in smokers and nonsmokers: results of a randomized, placebo-controlled phase 1/2 trial. Nicotine Tob. Res. 2008, 10, 213-8.
(10) Hatsukami, D. K.; Jorenby, D. E.; Gonzales, D.; Rigotti, N. A.; Glover, E. D.; Oncken, C. A.; Tashkin, D. P.; Reus, V. I.; Akhavain, R. C.; Fahim, R. E.; Kessler, P. D.; Niknian, M.; Kalnik, M. W.; Rennard, S. I. Immunogenicity and smoking-cessation outcomes for a novel nicotine immunotherapeutic. Clin. Pharmacol. Ther. 2011, 89, 392-9.
(11) Hoogsteder, P.; Kotz, D.; Viechtbauer. W.; Brauer. R.; Kessler, P.; Kalnik. M.; Fahim. R.; Spiegel, P. V.; Schayck, O. V. The efficacy and safety of a nicotine conjugate vaccine (NicVAX®) or placebo co-administered with varenicline (Champix®) for smoking cessation: study protocol of a phase IIb, double blind, randomized, placebo controlled trial. BMC Public Health 2012, 12, 1052.
(12) Nabi Biopharmaceuticals announces results of first NicVAX phase III clinical trial: smoking cessation immunotherapy failed to meet primary endpoint. Nabi Biopharmaceuticals: Rockville, Md., Jul. 18, 2011.
(13) Nabi Biopharmaceuticals announces results of second NicVAX phase III clinical trial: smoking cessation immunotherapy failed to meet primary endpoint. Nabi Biopharmaceuticals: Rockville, Md., Nov. 7, 2011.
(14) Selecta Biosciences initiates phase 1 clinical study of SEL-068, a first-in-class synthetic nicotine vaccine for smoking cessation and relapse prevention. Selecta Biosciences: Watertown, Mass., Nov. 21, 2011.
(15) Pittet, L.; Altreuter, D.; Ilyinskii, P.; Fraser, C.; Gao, Y.; Baldwin, S.; Keegan, M.; Johnston, L.; Kishimoto, T. Development and preclinical evaluation of SEL-068, a novel targeted Synthetic Vaccine Particle (tSVP™) for smoking cessation and relapse prevention that generates high titers of antibodies against nicotine. J. Immunol. 2012, 188.
(16) Lockner, J. W.; Ho, S. O.; McCague. K. C.; Chiang, S. M.; Do, T. Q.; Fujii, G.; Janda, K. D. Enhancing nicotine vaccine immunogenicity with liposomes. Bioorg. Med. Chem. Lett. 2013, 23, 975-8.
(17) McCluskie, M. J.; Pryde, D. C.; Gervais, D. P.; Stead, D. R.; Zhang, N.; Benoit, M.; Robertson, K.; Kim, I. J.; Tharmanathan, T.; Merson, J. R.; Davis, H. L. Enhancing immunogenicity of a 3'aminomethylnicotine-DT-conjugate anti-nicotine vaccine with CpG adjuvant in mice and non-human primates. Int. Immunopharmacol. 2013, 16, 50-56.
(18) Chen, X.; Pravetoni, M.; Bhayana, B.; Pentel, P. R.; Wu, M. X. High immunogenicity of nicotine vaccines obtained by intradermal delivery with safe adjuvants. Vaccine 2012.
(19) Kevler, D. E.; Roiko, S. A.; Earley, C. A.; Murtaugh, M. P.; Pentel, P. R. Enhanced immunogenicity of a bivalent nicotine vaccine. Int. Immunopharmacol. 2008, 8, 1589-94.
(20) Pravetoni, M.; Keyler, D. E.; Pidaparthi, R. R.; Carroll. F. I.; Runyon, S. P.; Murtaugh, M. P.; Earley, C. A.; Pentel, P. R. Structurally distinct nicotine immunogens elicit antibodies with non-overlapping specificities. Biochem. Pharmacol. 2012, 83, 543-50.
(21) de Villiers, S. H.; Comish, K. E.; Troska, A. J.; Pravetoni, M.; Pentel, P. R. Increased efficacy of a trivalent nicotine vaccine compared to a dose-matched monovalent vaccine when formulated with alum. Vaccine 2013, 31, 6185-93.

(22) Comish, K. E.; de Villiers, S. H.; Pravetoni, M.; Pentel, P. R. Immunogenicity of individual vaccine components in a bivalent nicotine vaccine differ according to vaccine formulation and administration conditions. PLoS ONE 2013, 8, e82557.

(23) Berzofsky. J. A.; Schechter, A. N. The concepts of crossreactivity and specificity in immunology. Mol. Immunol. 1981, 18, 751-63.

(24) Nowak, M. A. Immune responses against multiple epitopes: A theory for immunodominance and antigenic variation. Semin. Virol. 1996, 7, 83-92.

(25) Langman, R. E. The specificity of immunological reactions. Mol. Immunol. 2000, 37, 555-61.

(26) Skibinski, D. A.; Baudner, B. C.; Singh, M.; O'Hagan, D. T. Combination vaccines. J. Glob. Infect. Dis. 2011, 3, 63-72.

(27) Andrews, N. J.; Waight, P. A.; George, R. C.; Slack, M. P.; Miller, E. Impact and effectiveness of 23-valent pneumococcal polysaccharide vaccine against invasive pneumococcal disease in the elderly in England and Wales. Vaccine 2012, 30, 6802-8.

(28) Landsteiner, K.; van der Scheer, J. Serological differentiation of steric isomers. J. Exp. Med. 1928, 48, 315-20.

(29) Landsteiner, K. The Specificity of Serological Reactions. Charles C. Thomas: Springfield, Ill., 1936.

(30) Napper, A. D.; Benkovic, S. J.; Tramontano, A.; Lerner, R. A. A stereospecific cyclization catalyzed by an antibody. Science 1987, 237, 1041-3.

(31) Benkovic, S. J.; Napper, A. D.; Lemer, R. A. Catalysis of a stereospecific bimolecular amide synthesis by an antibody. Proc. Natl. Acad. Sci. U.S.A 1988, 85, 5355-8.

(32) Janda, K. D.; Benkovic, S. J.; Lemer, R. A. Catalytic antibodies with lipase activity and R or S substrate selectivity. Science 1989, 244, 437-40.

(33) Bjercke, R. J.; Cook. G.; Rychlik, N.; Gjika, H. B.; Van Vunakis, H.; Langone, J. J. Stereospecific monoclonal antibodies to nicotine and cotinine and their use in enzyme-linked immunosorbent assays. J. Immunol. Methods 1986, 90, 203-13.

(34) Paula, S.; Tabet, M. R.; Farr, C. D.; Norman, A. B.; Ball, W. J., Jr. Three-dimensional quantitative structure-activity relationship modeling of cocaine binding by a novel human monoclonal antibody. J. Med. Chem. 2004, 47, 133-42.

(35) Treweek, J. B.; Roberts, A. J.; Janda, K. D. Immunopharmacotherapeutic manifolds and modulation of cocaine overdose. Pharmacol., Biochem. Behav. 2011, 98, 474-84.

(36) Treweek, J. B.; Janda, K. D. An antidote for acute cocaine toxicity. Mol. Pharmaceutics 2012, 9, 969-78.

(37) Isomura, S.; Wirsching, P.; Janda. K. D. An immunotherapeutic program for the treatment of nicotine addiction: hapten design and synthesis. J. Org. Chem. 2001, 66, 4115-21.

(38) Meijler. M. M.; Matsushita, M.; Altobell, L. J., 3rd; Wirsching, P.; Janda, K. D. A new strategy for improved nicotine vaccines using conformationally constrained haptens. J. Am. Chem. Soc. 2003, 125, 7164-5.

(39) Moreno, A. Y.; Azar. M. R.; Warren, N. A.; Dickerson, T. J.; Koob, G. F.; Janda, K. D. A critical evaluation of a nicotine vaccine within a self-administration behavioral model. Mol. Pharmaceutics 2010, 7, 431-41.

(40) Pentel, P. R.; Malin. D. H.; Ennifar, S.; Hieda, Y.; Keyler, D. E.; Lake, J. R.; Milstein, J. R.; Basham, L. E.; Coy, R. T.; Moon, J. W.; Naso. R.; Fattom, A. A nicotine conjugate vaccine reduces nicotine distribution to brain and attenuates its behavioral and cardiovascular effects in rats. Pharmacol., Biochem. Behav. 2000, 65, 191-8.

(41) Pryde. D. C.; Jones, L. H.; Gervais, D. P.; Stead, D. R.; Blakemore, D. C.; Selby, M. D.; Brown, A. D.; Coe, J. W.; Badland, M.; Beal, D. M.; Glen, R.; Wharton, Y.; Miller, G. J.; White, P.; Zhang, N.; Benoit, M.; Robertson, K.; Merson, J. R.; Davis, H. L.; McCluskie, M. J. Selection of a novel anti-nicotine vaccine: influence of antigen design on antibody function in mice. PLoS ONE 2013, 8, e76557.

(42) Davis, H. L.; Weeratna, R; Waldschmidt, T. J.; Tygrett. L.; Schorr, J.; Krieg, A. M. CpG DNA is a potent enhancer of specific immunity in mice immunized with recombinant hepatitis B surface antigen. J. Immunol. 1998, 160, 870-6.

(43) Hartmann, G.; Weeratna, R. D.; Ballas, Z. K.; Payette, P.; Blackwell, S.; Suparto, I.; Rasmussen. W. L.; Waldschmidt. M.; Sajuthi, D.; Purcell, R. H.; Davis, H. L.; Krieg, A. M. Delineation of a CpG phosphorothioate oligodeoxynucleotide for activating primate immune responses in vitro and in vivo. J. Immunol. 2000, 164, 1617-24.

(44) Bremer, P. T.; Schlosburg, J. E.; Lively, J. M.; Janda, K. D. Injection route and TLR9 agonist addition significantly impact heroin vaccine efficacy. Mol. Pharmaceutics 2014, 11, 1075-80.

(45) Cervi, L.; Borgonovo, J.; Egea, M.; Chiapello, L.; Masih, D. Immunization of rats against *Fasciola hepatica* using crude antigens conjugated with Freund's adjuvant or oligodeoxynucleotides. Vet. Immunol. Immunopathol. 2004, 97, 97-104.

(46) Muller, R. Determination of affinity and specificity of anti-hapten antibodies by competitive radioimmunoassay. Methods Enzymol. 1983, 92, 589-601.

(47) Tars, K.; Kotelovica, S.; Lipowsky, G.; Bauer, M.; Beerli, R. R.; Bachmann, M. F.; Maurer, P. Different binding modes of free and carrier-protein-coupled nicotine in a human monoclonal antibody. J. Mol. Biol. 2012, 415, 118-127.

(48) Beerli. R. R.; Bauer, M.; Buser, R. B.; Gwerder, M.; Muntwiler, S.; Maurer, P.; Saudan, P.; Bachmann, M. F. Isolation of human monoclonal antibodies by mammalian cell display. Proc. Natl. Acad. Sci. U.S.A 2008, 105, 14336-41.

(49) Spector, S.; Parker, C. W. Morphine: radioimmunoassay. Science 1970, 168, 1347-8.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A process for preparing a compound according to the formula (−)-N4N:

comprising the steps of:
(A) contacting (−)-(S)-nicotine sequentially with (i) trimethylacetyl chloride and (ii) a combination of (3-ethoxy-3-oxopropyl)zinc(II) iodide, lithium chloride, and copper cyanide to yield a compound according to formula 3:

(B) contacting the compound according to formula 3 with sulfur to yield a compound according to formula 4:

(C) contacting the compound according to formula 4 with NH₄OH to yield a compound according to formula 5:

and
(D) contacting the compound according to formula 5 with sodium bis(2-methoxyethoxy)aluminum hydride to yield the compound according to formula (−)-N4N.

2. The process according to claim 1, wherein the contacting of step (A) occurs in THF.

3. The process according to claim 1 or 2, wherein the molar ratio of (−)-(S)-nicotine to (i) trimethylacetyl chloride is 1:1.

4. The process according to claim 1, wherein step (B) occurs in refluxing toluene.

5. The process according to claim 1, wherein in step (B) the molar ratio of sulfur to the compound according to formula 3 is 1.3:1.

6. The process according to claim 1, wherein step (D) occurs in toluene.

7. The process according to claim 1, wherein in step (D) the molar ratio of sodium bis(2-methoxyethoxy)aluminum hydride to the compound according to formula 5 is 4.5:1.

* * * * *